United States Patent [19]

Uwajima et al.

[11] Patent Number: 4,981,788

[45] Date of Patent: Jan. 1, 1991

[54] NOVEL ACETYLPOLYAMINE AMIDOHYDROLASE

[75] Inventors: Takayuki Uwajima; Kinya Fujishiro, both of Machida; Mayumi Ando, Yokohama, all of Japan

[73] Assignee: Kyowa Hakko Kogyo Co., Ltd., Tokyo, Japan

[21] Appl. No.: 212,654

[22] Filed: Jun. 28, 1988

[30] Foreign Application Priority Data

Jun. 30, 1987 [JP] Japan ................... 62-163821

[51] Int. Cl.$^5$ ................... C12Q 1/34; C12N 9/80
[52] U.S. Cl. ................... 435/18; 435/228; 435/814; 435/815
[58] Field of Search ................... 435/18, 228, 814, 815

[56] References Cited

FOREIGN PATENT DOCUMENTS 7435 2/1984 Japan .
98982 3/1985 Japan .
43380 6/1985 Japan .

OTHER PUBLICATIONS

Okada et al, Polyamines: Basic and Clinical Aspects, 1985, pp. 72–80.
Chemical Abstracts, vol. 103, 1985, Meito Sangyo Co., Ltd., p. 410, 36189c, "Manufacture of N-Acetylpolyamine amidohydrolase m".

*Primary Examiner*—Esther M. Kepplinger
*Assistant Examiner*—Laurie A. Scheiner
*Attorney, Agent, or Firm*—Fitzpatrick, Cella, Harper & Scinto

[57] ABSTRACT

A novel acetylpolyamine amidohydrolase is described. The enzyme specifically hydrolyzes the amino bond in acetylputrescine, acetylcadaverine, acetylspermidine and acetylspermine with strong substrate affinity. The enzyme is preferably produced by culturing a microorganism belonging to the genus Mycoplana, and is used in the quantitative determination of polyamine contained in a living body sample, which is useful for cancer diagnosis.

5 Claims, 7 Drawing Sheets

NOVEL ACETYLPOLYAMINE AMIDOHYDROLASE

BACKGROUND OF THE INVENTION

The present invention relates to a new acetylpolyamine amidohydrolase, to a process for producing the same, and to a method for quantitative determination of acetylpolyamine by using the same.

Polyamine is the generic name of putrescine, cadaverine, spermidine and spermine which are basic substances widely distributed in living bodies. Since Russel reported that the urine of cancer patients contains the polyamine in unusually large quantities (Cancer Res., 31, 1555, 1971), detection of polyamine has been applied to the diagnosis of cancer. Its quantitative determination is useful in the auxiliary cancer diagnosis and for the monitoring of the therapeutical effect of anticancer agents.

Electrophoresis, thin-layer chromatography (dansyl method), gas chromatography, high-performance liquid chromatography (HPLC) and analysis by means of an amino-acid analyzer have been used for the quantitative determination of the polyamine. However, in the quantitative determination of the polyamine contained in the urine, which exists for the most part in the form of acetyl derivative, the derivative must be hydrolyzed with hydrochloric acid into the corresponding free polyamine prior to analysis. This pretreatment is intricate in operation and detracts from the rapidity of analytical process. Enzymes capable of hydrolyzing acetylpolyamines (acetylpolyamine amidohydrolases), derived from *Streptomyces avellanius* (Japanese Published Unexamined Patent Application No. 144088/1981), *Arthrobacter sp.* (Japanese Published Unexamined Patent Application No. 43380/1985) and *Micrococcus luteus* (Japanese Published Unexamined Patent Application No. 98982/1985) have been known so far.

However, all the enzymes so far known are specific to acetylputrescine, and weak in acting upon other types of acetylpolyamine. Since the urine also contains acetylspermidine, acetylcadaverine and acetylspermine in significant quantities in addition to acetylputrescine, there has been a demand for a new type of enzyme which is capable of hydrolyzing these substrates with strong substrate affinity.

Intensive studies in search of a new acetylpolyamine amidohydrolase capable of acting upon many types of acetylpolyamines have led us to find that a microorganism belonging to the genus Mycoplana produces such an enzyme. The novel enzyme is different from known acetylpolyamine amidohydrolases in many properties, particularly in substrate specificity.

SUMMARY OF THE INVENTION

According to the present invention, a novel acetylpolyamine amidohydrolase having the following characteristics is provided:

(i) molecular weight: 67,000 by a gel filtration method using high-performance liquid chromatography, the enzyme being of a dimeric structure composed of two subunits having a molecular weight of 36,000 by SDS-polyacrylamide gel electrophoresis, (ii) isoelectric point: 4.56 by isoelectricfocusing, (iii) optimum pH: at pH 9 for acetylputrescine and acetylspermidine, at about pH 8 for acetylcadaverine; at pH 10 for acetylspermine, (iv) optimum temperature: 60° C., (v) substrate specificity: the enzyme specifically hydrolyzes the amide bond in acetylputrescine, acetylcadaverine, acetylspermidine and acetylspermine, and (vi) inhibitor: the enzyme is inhibited by $Zn^{2+}$, 8-oxyquinoline and $Ag^+$.

The acetylpolyamine amidohydrolase of the present invention is preferably produced by culturing a microorganism belonging to the genus Mycoplana.

BRIEF DESCRIPTION OF THE DRAWINGS

In FIG. 1, X, ▲, □ and . represent the relative activity for acetylputrescine, acetylcadaveri $N^1$-acetylspermidine, $N^8$-acetylspermidine and acetylspermine, respectively.

DESCRIPTION OF THE INVENTION

The novel acetylpolyamine amidohydrolase of the present invention (hereinafter referred to as "the present enzyme" in some cases) is characterized by its strong affinity for acetylputrescine, acetylcadaverine, acetylspermidine and acetylspermine. As the acetylspermidine, $N^1$-acetylspermidine and $N^8$-acetylspermidine are known The present enzyme is capable of acting on both of them.

The present enzyme includes both a product purified to homogeneity and a partially purified product of the enzyme exhibiting the above-mentioned characteristic.

Shown below are the physicochemical properties of the partially purified product obtained in Example 2 described hereinafter.

(Measurement of enzyme activity)

Activity of the present enzyme (partially purified products) is measured according to the following procedure. That is, 0.1 ml of an enzyme solution is added to a reagent solution consisting of 1.5 ml of 0.1 M phosphate buffer (pH 7.0), 0.05 ml of 50 mM acetylpolyamine, 0.4 U of putrescine oxidase (when acetylputrescine, acetylcadaverine or acetylspermidine is used as substrate) or polyamine oxidase (when acetylspermidine or acetylspermine is used as substrate), 0.5 ml of 2.4 mM 4-aminoantipyrine, 0.5 ml of 42 mM phenol and 20 U of peroxidase. The mixture is incubated at 37° C., and the absorbance of quinoneimine pigment formed at 500 nm is measured.

In terms of the enzyme activity, the amount of enzyme that can hydrolyze 1 μmole of a substrate in one minute is defined as one unit (1 U). What should be noticed here is that two moles of hydrogen peroxide is formed from one mole of substrate by the action of polyamine oxidase when acetylspermine is used as substrate and by the action of putrescine oxidase when acetylspermidine is used as substrate, and hence this must be taken into consideration in calculating the enzyme activity.

(1) Substrate specificity

The relative activities of acetylpolyamine amidohydrolases against various type of acetylpolyamine, defining the activities against acetylputrescine as 100 under a condition of pH 7.0, are as shown in Table 1 below.

TABLE 1

| Substrate Specificity | | | | |
|---|---|---|---|---|
| | The present enzyme | $E_1$ | $E_2$ | $E_3$ |
| Acetylputrescine | 100% | 100% | 100% | 100% |
| Acetylcadaverin | 71 | — | 45 | 12.5 |
| $N^1$-Acetylspermidine | 108 | — | — | 3.5 |
| $N^8$-Acetylspermidine | 51 | 9.1* | 30* | 85.1 |
| Acetylspermine | 24 | 0.4 | 3 | 2.1 |

Figure 1:
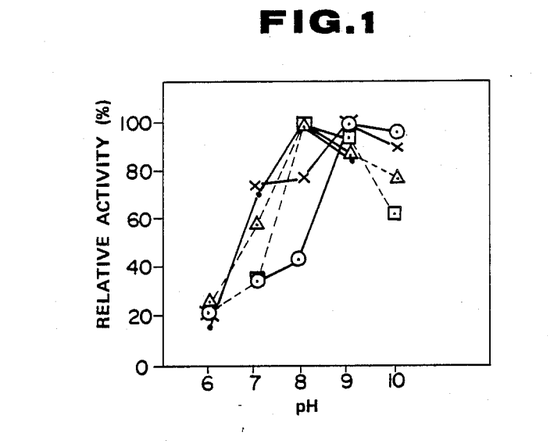
FIG. 1 is a graph showing the optimum pH for partially purified product of the enzyme of the present invention.

$E_1$: Enzyme derived from *Streptomyces avellaneus*
$E_2$: Enzyme derived from *Arthrobacter sp.*
$E_3$: Enzyme derived from *Micrococcus luteus*
*Acetylspermidine (2) Optimum pH Enzyme activity was measured at different pH levels ranging from 6 to 10 by using bis-Tris propane buffer solutions. The optimum pH was 9 for acetylputrescine and acetylcadaverine, and 8 for $N^1$-acetylspermidine, $N^8$-acetylspermidine and acetylspermine, as shown in FIG. 1.

(3) Stability (pH Stability)

Figure 2:
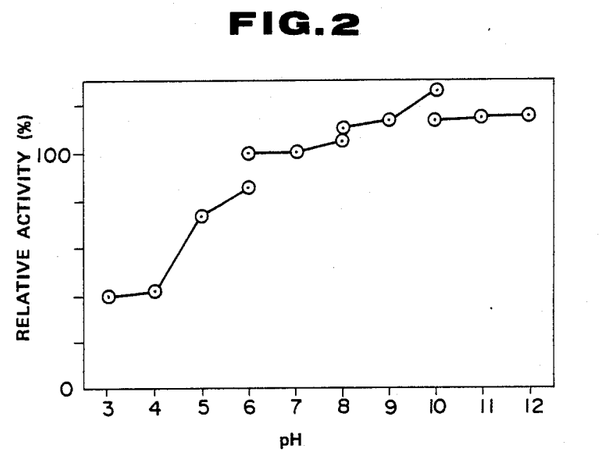
FIG. 2 is a graph showing pH stability of the partially purified product of the enzyme of the present invention.

The present enzyme was incubated at 37° C. for 30 minutes at different pH levels, using citrate buffers for pH 3 to 6, phosphate buffers for pH 6 to 8, bis-Tris propane buffers for pH 8 to 10, and borate/KCl buffers for pH 10 to 12, and then the residual activity was measured using acetylputrescine as substrate. The result is shown in FIG. 2, which indicates that the enzyme remains stable within the pH range between 6 and 12.

(Thermal stability)

Figure 3:
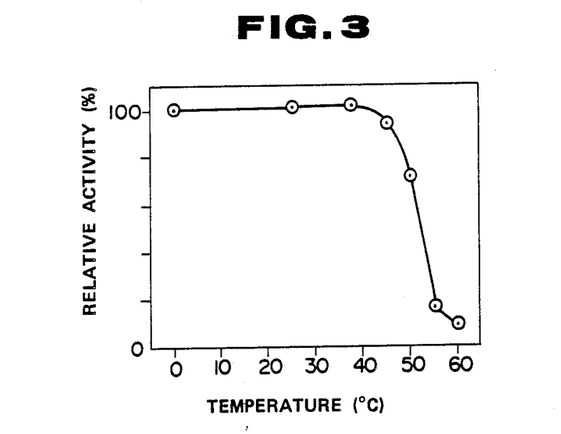
FIG. 3 is a graph showing thermal stability of the partially purified product of the enzyme of the present invention.

The present enzyme was incubated in a phosphate buffer at pH 7.0 at different temperatures for 30 minutes, and the residual activity was measured using acetylputrescine as substrate. The result is shown in FIG. 3, which indicates that the enzyme is stable at temperatures up to 45° C.

TABLE 2

| pH and Thermal Stability | | | | |
|---|---|---|---|---|
| | The present enzyme | $E_1$ | $E_2$ | $E_3$ |
| pH Stability | 6~12 | 6.5~8.5 | 6~8 | 7~9 |
| Thermal stability | ~45° C. | ~35° C. | ~35° C. | ~40° C. |

$E_1$, $E_2$ and $E_3$ are as defined in Table 1.

As in apparent from the table, the present enzyme is superior to the other known acetylpolyamine amidohydrolases in both pH and thermal stabilities.

(4) Optimum temperature

Figure 4:
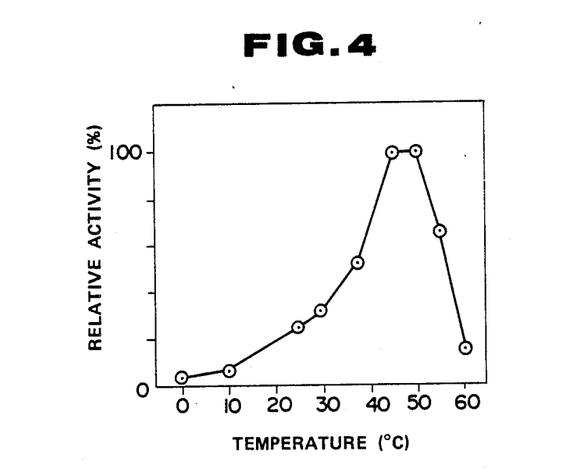
FIG. 4 is a graph showing the optimum temperature for partially purified product of the enzyme of the present invention.

The optimum working temperature for the present enzyme was about 50° C., when the relative activity was determined, using acetylputrescine as substrate, as shown in FIG. 4. The optimum temperatures for the other acetylpolyamine amidohydrolases were 30° to 40° C. This clearly distinguishes the present enzyme from the known enzymes.

(5) Effects of inhibitors and metal ions

The effects of various inhibitors and metal ions upon the present enzyme and the other known enzymes were examined using acetylputrescine as substrate. The result is shown in Table 3.

TABLE 3

| Concentration of 1mM | The present enzyme | $E_1$ | $E_2$ | $E_3$ |
|---|---|---|---|---|
| — | 100% | 100% | 100% | 100% |
| Hydroxylamine | 24 | — | — | — |
| pCMB | 4 | 0 | 8 | 98 |
| DDC | 0 | — | — | — |
| 8-Hydroxyquinoline | 3 | — | — | 98 |
| o-Phenanthroline | 68 | 14 | 94 | 33 |
| $NaN_3$ | 90 | 93 | 99 | 98 |
| $Cu^{2+}$ | 99 | — | — | 26 |
| $Zn^{2+}$ | 100 | 3 | 32 | 4 |
| $Mn^{2+}$ | 124 | 82 | 101 | 50 |
| $Mg^{2+}$ | 97 | 104 | 112 | 99 |
| $Ni^{2+}$ | 81 | 3 | 55 | 33 | pCMB: p-(Chloromercuri)benzoic acid
DDC: Diethyldithiocarbamate
$E_1$, $E_2$ and $E_3$ are as defined in Table 1.

As seen from the table, the present enzyme is hardly inhibited by zinc and nickel, while the other known enzymes are markedly inhibited by these metals.

(6) $K_m$ values $K_m$ values of the present enzyme and the other known enzymes for various types of acetylpolyamine at pH 7.0 were determined from the Line weaver-Burk plot [refer to J. Am. Chem. Soc., 56, 658 (1934)]. The result is shown in Table 4.

TABLE 4

| $K_m$ Values for Acetylpolyamine | | | | |
|---|---|---|---|---|
| | The present enzyme | $E_1$ | $E_2$ | $E_3$ |
| Acetylcadaverine | 0.13 | — | 1.60 | — |
| $N^1$-Acetylspermidine | 0.27 | 1.1* | 0.50* | — |
| $N^8$-Acetylspermidine | 0.56 | — | — | 0.38 |
| Acetylspermine | 0.16 | — | — | — |

* Acetylspermidine
$E_1$, $E_2$ and $E_3$ are as defined in Table 1.

As seen from the table, the present enzyme has smaller $K_m$ values than those of the other known enzymes. Therefore the present enzyme has a strong affinity for acetylpolyamine, and is suitable for the quantitative determination of acetylpolyamine by the end-point assay [S. Shimizu, et al., "Enzymatic Analysis - Principle and Application", p44 (1977)].

(7) Molecular weight

The molecular weight of the present enzyme was determined to be 44,000 by gel filtration method using HPLC Superose 12 (product of Pharmacia Fine Chemicals).

Next is shown the physicochemical properties of the product purified to homegeneity of the present enzyme obtained in Example 6 hereinafter. The enzyme activity of this product was measured according to the methods described below.

[Method 1] (Standard assay)

In this standard method for measuring the activity of acetylpolyamine amidohydrolases, the enzyme being tested is allowed to react with acetylputrescine as substrate to produce putrescine, which is in turn oxidized with putrescine oxidase. Hydrogen peroxide thus formed is then subjected to oxidative condensation with phenol and 4-aminoantipyrine in the presence of horseradish peroxidase to form quinoneimine pigment. The rate of increase in the absorbance of a colored reaction solution at 500 nm is measured with a spectrophotometer.

The reactions involved may be expressed by the following equations (1), (2) and (3):

$$\text{Acetylputrescine} + H_2O \xrightarrow{\text{Acetylpolyamine amidohydrolase}} \text{Putrescine} + CH_3COOH \quad (1)$$

$$\text{Putrescine} + O_2 + H_2O \xrightarrow{\text{Putrescine oxidase}} \text{4-Aminobutyladehyde} + H_2O_2 \quad (2)$$

$$2H_2O_2 + \text{Phenol} + \text{4-Aminoantipyrine} \xrightarrow{\text{Horseradish peroxidase}} \text{Quinoneimine} + 4H_2O \quad (3)$$

(1) Reagents

| | |
|---|---|
| (a) Substrate: 50 mM aqueous acetylputrescine solution | 0.05 ml |
| (b) Buffer solution: 100 mM borate buffer (pH 10.0) (containing 100 mM KCl) | 0.5 ml |
| (c) 4-Aminoantipyrine: 2.4 mM aqueous solution | 0.5 ml |
| (d) Phenol: 42 mM aqueous solution | 0.5 ml |
| (e) Horseradish peroxidase (200 U/ml): Solution in 50 mM phosphate buffer (pH 7.5) | 0.1 ml |
| (f) Putrescine oxidase (20 U/ml): Solution in 50 mM phosphate buffer (pH 7.5) | 0.05 ml |
| (g) Distilled water | 1.2 ml |
| (h) Enzyme solution | 0.1 ml |

(2) Procedure

The above reagents, (b) through (h), were put in a cuvette (d: 1.0 cm) and the mixture was preincubated at 37° C. for 2 minutes. The substrate solution (a) was then added and the resulting mixture was held at 37° C., absorbance at 500 nm was measured over a period of 3 to 5 minutes, and the change in absorbance per minute ($\Delta OD_{sample}$) was determined from the linear portion of the plotted curve. For control, the same procedure as above was carried out, using distilled water as reference.

(3) Calculation of potency

One unit of acetylpolyamine amidohydrolase is defined as its amount necessary to hydrolyze 1 μmole of acetylputrescine at 37° C. for one minute (or the amount necessary to form 0.5 μmole of quinoneimine pigment formed in the method for measuring the enzyme activity described above).

Since it was reported that the extinction coefficient of 0.5 mM quinoneimine is 5.33 [Clin. Chem., 20/4, 470–475 (1974)], the potency (A) for 1 ml of the enzyme solution may be calculated from the following equation:

$$(A) = \Delta OD_{sample} \times 3/(5.33 \times 0.1)$$

$$= \Delta OD_{sample} \times 5.63 \text{(unit/ml)}$$

[Method 2] (Assay when acetylputrescine, acetylcadaverine, $N^1$-acetylspermidine and $N^8$-acetylspermidine are used as substrate:)

The acetylpolyamine can be hydrolyzed by the acetylpolyamine amidohydrolase, as described in [Method 1], and the corresponding free polyamine thus formed is then oxidized by putrescine oxidase. Putrescine oxidase derived from *Micrococcus rubens* is known to have an activity upon putrescine, cadaverine and spermidine [Adachi, et al., Agric. Biol. Chem, 30, 1202 (1966)]. This oxidase specifically acts upon a free form of polyamine to form an equimolar amount of hydrogen peroxide, and hence can be used for the intended quantitative analysis. The actual analytical procedure is as described below.

(1) Reagents

| | |
|---|---|
| (a) Substrate: 50, 25, 12.5, 6.25 or 3.125 mM aqueous acetylputrescine, acetylcadaverine, $N^1$-acetylspermidine or $N^8$-acetylspermidine solution | 0.1 ml |
| (b) Buffer solution: 100 mM phosphate buffer (pH 9.0) | 1.5 ml |
| (c) 4-Aminoantipyrine: 2.4 mM aqueous solution | 0.5 ml |
| (d) Phenol: 42 mM aqueous solution | 0.5 ml |
| (e) Horseradish peroxidase (200 U/ml): Solution in 50 mM phosphate buffer (pH 7.5) | 0.1 ml |
| (f) Putrescine oxidase (27 U/ml): Solution in 50 mM phosphate buffer (pH 7.5) | 0.1 ml |
| (g) Distilled water | 0.1 ml |
| (h) Solution of the present enzyme | 0.1 ml |

(2) Procedure

The above reagents, (b) through (h), were put in a cuvette (d: 1.0 cm) and the mixture was preincubated at 37° C. for 2 minutes. The substrate solution (a) was then added, and the resulting mixture was incubated at 37° C. Absorbance at 500 nm was measured over a period of 3 to 5 minutes, and the change in absorbance per minute ($\Delta OD_{sample}$) was determined from the linear portion of the plotted curve. For control, the same procedure as above was carried out, using distilled water as reference.

(3) Calculation of potency

One unit of acetylpolyamine amidohydrolase is defined as its amount necessary to hydrolyze 1 μmole of acetylputrescine at 37° C. for one minute (or the amount necessary to form 0.5 μmole of quinoneimine pigment formed in the method for measuring the enzyme activity described above).

Since it was reported that the extinction coefficient of 0.5 mM quinoneimine is 5.33, the potency (A) for 1 ml of the enzyme solution may be calculated from the following equation:

$$(A) = \Delta OD_{sample} \times 3/(5.33 \times 0.1)$$

$$= \Delta OD_{sample} \times 5.63 \text{ (unit/ml)}$$

[Method 3] (Assay when acetylspermine is used as substrate:)

Acetylspermine is hydrolyzed by the action of acetylpolyamine amidohydrolase into free form of spermine. The free form of spermine can be oxidized by a polyamine oxidase derived from *Aspergillus terreus* to produce hydrogen peroxide. Two molar equivalents of hydrogen peroxide is formed from one molar equivalent of spermine. Thus, the enzyme activity can be measured by quantitative determination of the hydrogen peroxide according to the method described above. However, since the above polyamine oxidase also acts upon acetylspermine, it is impossible to exactly measure the activity of acetylpolyamine amidohydrolase by the standard assay. Hence, it is necessary that the reaction mixture after hydrolysis is subjected to HPLC to separate free form of spermine from acetylspermine, the fraction containing only free form of spermine is allowed to react with polyamine oxidase, and hydrogen peroxide thus formed is quantitatively determined by the above-described method. The actual procedure is described below.

| (1) Reagent (for enzyme reaction) | |
|---|---|
| (a) Substrate: 50, 25, 12.5, 6.25 and 3.125 mM aqueous acetylspermine solution | 5 μl |
| (b) Buffer solution: 100 mM phosphate buffer (pH 9.0) | 75 μl |
| (c) Solution of the present enzyme | 10 μl |
| (d) Distilled water | 60 μl |
| (e) Reaction terminator: 20% (w/v) aqueous trichloroacetic acid solution | 30 μl |
| (2) Reagents (for enzyme activity measurement) | |
| (a) Buffer solution: 0.5 M phosphate buffer (pH 6.0) | 0.3 ml |
| (b) 0.5% (w/v) aqueous Triton X-100 solution | 2.31 ml |
| (c) 42 mM aqueous phenol solution | 80 μl |
| (d) 5.0% (w/v) aqueous bis[3-bis(4-chlorophenyl) methyl-4-dimethylaminophenyl)amine solution | 6 μl |
| (e) Polyamine oxidase (250 U/ml) | 4 μl |
| (f) Horseradish peroxidase (200 U/ml) | 0.1 ml |

(3) Reagents (for HPLC)

(a) Eleunt A: A solution of 0.1 M sodium acetate in 1 liter of distilled water is adjusted to pH 4.5 by addition of glacial acetic acid, and sodium 1-octanesulfonate is added to a concentration of 10 mM.

(b) Eluent B: A solution of 0.2 M sodium acetate in 1 liter of distilled water was adjusted to pH 4.5 by addition of glacial acetic acid, and sodium 1-octanesulfonate is added to a concentration of 10 mM, followed by admixture of 300 ml of acetonitrile therewith.

(4) Instruments used (a) Column for HPLC: μBondapak (product of Waters); C18, φ3.9 mm×300 mm (b) Precolumn for HPLC: Guardpak μBondapak (Product of Waters)

(c) Pumps: High-pressure mixing system composed of two Model 880-PU pumps (product of Nihon Bunko)

(d) Thermostatic chamber: Model 860-30 (product of Nihon Bunko)

(e) Sample injector: Loop injector (capacity: 100 μl)

(f) Fraction collector: Model FC-203 (product of Gilson)

(5) Seperation of free form of spermine from acetylspermine by HPLC

The column and precolumn are equilibrated at 35° C. with Eluent A at a flow rate of 90 ml/hr for 6 minutes. Then, 100 μl of a sample solution was added thereto, linear gradient elution was carried out by using Eluent B (for 30 minutes at an eluent increase rate of 2%/min, and for 15 minutes at an increase rate of 4%/min), and fractions are collected in test tubes (0.75 ml in each).

(6) Procedure

Reagents (b) through (d) given in item (1) were put in a test tube and the mixture was preincubated at 37° C. for 2 minutes. The substrate solution (a) was then added, the resulting mixture was incubated at 37° C. for 10 minutes, and the reaction was stopped by addition of the termination (e). A sample solution (100 μl) was taken from the reaction mixture and subjected to HPLC as described above to separate free form of spermine from acetylspermine. Generally, acetylspermine is eluted at a position of 38 minutes after the start of elution and free form of spermine at a position of 41 minutes after the start of elution. A sample solution (200 μl), taken from the eluate containing free form of spermine, was mixed in a cuvette with reagents (a) through (e) given in item (2) above, the mixture was incubated at 37° C. for 10 minutes, and the absorbance at 755 nm was measured. For control, the same procedure as above was carried out using 200 μl of Elunt A in place of the sample solution, as reference.

(7) Calculation of potency

The concentration of free form of spermine in the reaction mixture can be determined from a calibration curve previously prepared on the basis of aqueous soluitons of free form of spermine with different concentrations. If the concentration of free form of spermine contained in 150 μl of the reaction mixture is taken as P (mM), then the potency (A) for 1 ml of the enzyme solution can be expressed by the following equation:

$$(A) = P \times 0.15 \times (1/0.01)/10 = P \times 1.5 (U/ml)$$

The reagents and instruments listed in items (2), (3) and (4) above were selected according to the method of Seiler, et al. [N. Seiler, et al., J. Chromatogr., 221, 227 (1980)].

1. Substrate specificity

The activities upon acetylputrescine, acetylcadaverine, $N^1$-acetylspermidine and $N^8$-acetylspermidine were measured by [Method 2] in a phosphate buffer (pH 9.0) at a substrate concentration of 0.833 mM, and the activity upon acetyl-spermine was measured by [Method 3] under the same conditions. Table 5 shows the relative activities when the activity upon acetylputrescine is taken as 100. $K_m$ values, determined from the Lineweaver-Burk plot, are also listed in the same table.

As reference, are shown the data reported for the acetylpolyamine amidohydrolase derived from *Streptomyces avellaneus*.

As seen from the table, the enzyme of the present invention acts upon a variety of substrates, the $K_m$ values being on the level of $10^{-4}$ to $10^{-5}$ M. In contrast, the acetylpolyamine amidohydrolase derived from *Streptomyces avellaneus* is weak at action on the other substrates than acetylputrescine, especially acetylspermine, and $K_m$ values are about 10 times as large as those of the present enzyme.

TABLE 5

| Substrate | Mycoplana bullate | | | St. avellaneus | |
|---|---|---|---|---|---|
| | Relative activity | $K_m$ | $V_{max}$[1] | Relative activity | $K_m$ |
| Acetylputrescine | 100% | 0.22 mM | 29.1 u/mg | 100% | 2.0 mM |
| Acetylcadaverine | 72 | 0.05 | 18.8 | — | — |
| $N^1$-Acetylspermidine | 61 | 0.13 | 20.5 | 9.1[2] | 1.1[2] |
| $N^8$-Acetylspermidine | 60 | 0.31 | 19.8 | | |
| Acetylspermine | 37 | 0.29 | 7.7 | 0.4 | — |

[1] Substrate inhibition at high concentrations was observed at 1 mM and higher for acetylputrescine, acetylcadaverine, $N^1$-acetylspermidine and $N^8$-acetylspermidine, and not observed even at 1.6 mM for acetylspermine.
[2] Acetylspermidine

2. Optimum pH and temperature (When acetylputrescine, acetylcadaverine and acetylspermidine are used as substrate:)

The effect of pH upon enzyme activity was examined by carrying out the enzyme reaction at 37° C. at different pH levels using phosphate buffers (for pH range from 7 to 9) and borate buffers (for pH range from 8 to 12). The activity was measured according to the procedure described in [Method 2] at a substrate concentration of 0.833 mM, with the amount of putrescine oxidase being varied in the range of 1 to 8 units depending on pH and the type of substrate used.

The effect of reaction temperature upon enzyme activity was examined by carrying out the enzyme reaction in 50 mM borate buffer (pH 8.5) at different temperatures (10°, 20°, 30°, 40°, 50°, 60° and 70° C.) and measuring the activity for 5 minutes after the start of reaction according to the above-mentioned procedure, with the amount of putrescine oxidase being varied in the range of 1 to 48 units.

(When acetylspermine is used as substrate:)

The pH and reaction temperature conditions were the same as described above, and enzyme activity was measured according to the procedure described in [Method 3].

Optimum pH

The optimum pH was 9 for acetylputrescine, $N^1$-acetylspermidine and $N^8$-acetylspermidine, about 8 for acetylcadaverine, and 10 for acetylspermine.

Optimum temperature

The optimum temperature was 60° C. for any of the acetylpolyamine tested.

3. Effects of pH and temperature upon stability

Incubation was carried out at 0° C. with acetylputrescine used as substrate at different pH levels (by use of phosphate and Tris-HCl buffers), the reaction sample was taken after a predetermined day, and the residual activity was measured according to the procedure described in [Method 1], thereby studying the effect of pH upon enzyme stability.

The effect of temperature upon enzyme stability was examined by carrying out incubation at 50° C. and 60° C. in a Tris-HCl buffer (pH 9.0) with acetylputrescine used as substrate, taking a sample solution after a predetermined time, and measuring the residual activity according to the procedure described in [Method 1].

pH Stability

Figure 9:
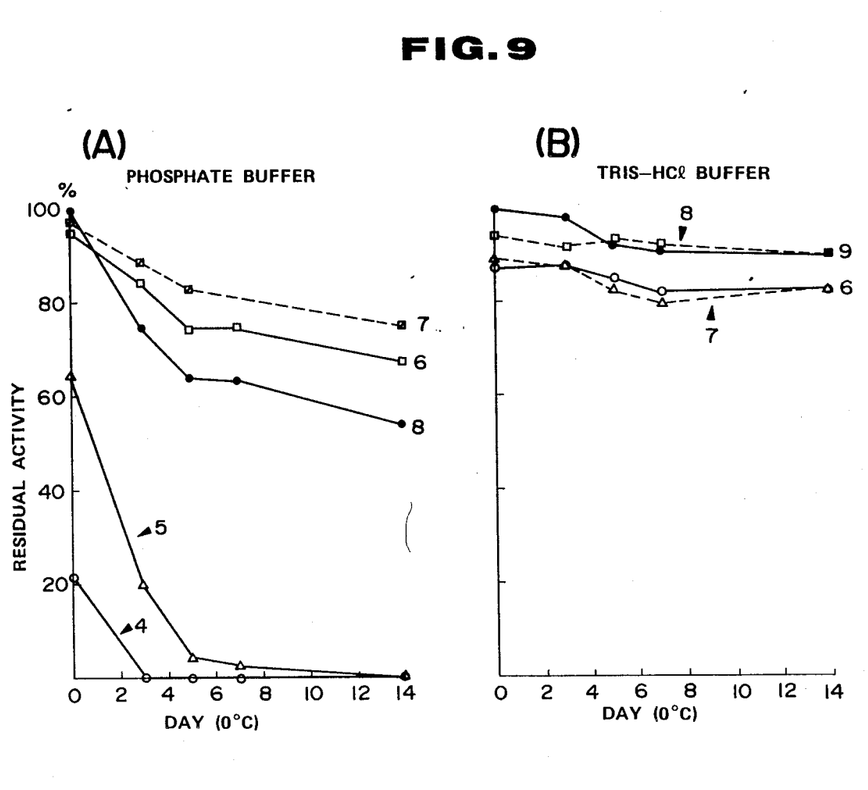
FIG. 9 is a graph showing pH stability of the product purified to homogeneity of the enzyme of the present invention.

As shown in FIG. 9, the present enzyme is stable within the pH range of 6 to 9, in Tris-HCl buffers. In particular, it remained stable even when stored for 2 weeks at a pH of 7 or higher. However, it is relatively unstable in phosphate buffers, being repidly inactivated at a pH of 5 or lower.

Thermal stability

Figure 10:
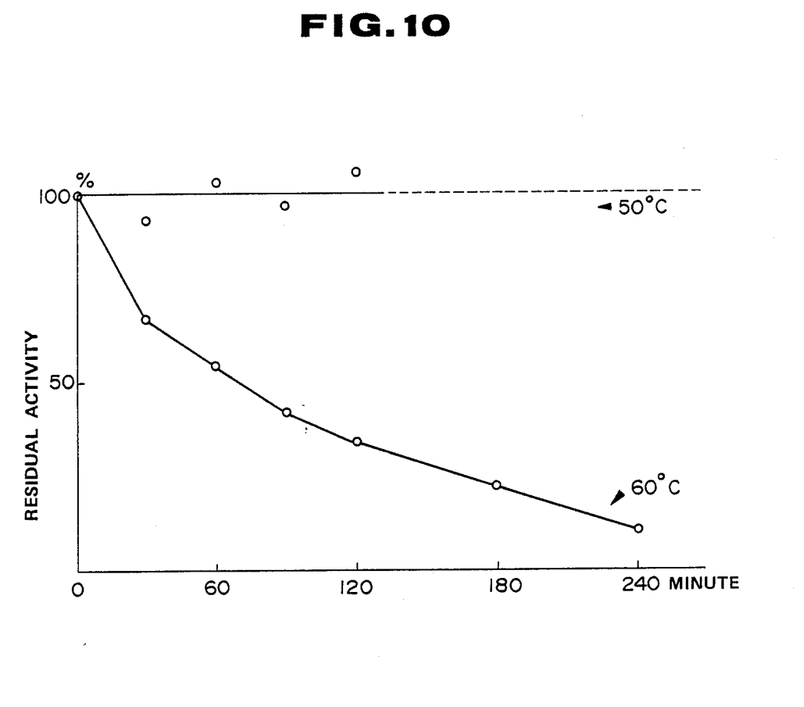
FIG. 10 is a graph showing thermal stability of the product purified to homogeneity of the enzyme of the present invention.

As shown in FIG. 10, the present enzyme remained stable for two hours or longer at 50° C., and 55% of the original activity was retained after one hour of incubation at 60° C. These results show that the present enzyme has high thermal stability.

4. Molecular weight

Molecular weight of the present enzyme in its native state, measured by gel filtration using HPLC under the conditions shown below, was 67,000—a value which approximately corresponds to the sedimentation coefficient $S_{20,w}$ (=5.27S). On the other hand, the molecular weight obtained by SDS-polyacrylamide gel electrophoresis was 36,000. This result suggests that the present enzyme is of a dimeric structure composed of two subunits having a molecular weight of 36,000.

| | |
|---|---|
| Column: | TSK G2000SW (product of Toyo Soda) |
| Pump: | 880-PU (product of Nihon Bunko) |
| Detector: | 875-UV (280 nm) (product of Nihon Bunko) |
| Loop injector: | Capacity: 20 μl |
| Flow rate: | 0.25 ml/min |
| Temperature: | Room temperature |
| Eluent: | 0.05 M Tris-HCl buffer (pH 7.0) containing 0.3 M NaCl |
| Standard proteins: | Cytochrome C (12.4K), adenylate kinase (32K), enolase (67K), lactate dehydrogenase (142K), glutamate dehydrogenase (290K) (all being products of Oriental Yeast Co., Ltd.) |

5. Metal contents in the present enzyme

Metal contents in a product purified to homogeneity of the present enzyme were measured using Hitachi Polarization Atomic-absorption Spectrophotometer (Model Z-8000; purchased from Nissei Sangyo), in which the frame method (p.17–282 and P.607–609 in "Latest Atomic-absorption Spectrophotometry" edited by K. Fuwa, et al.; published from Hirokawa Shoten in 1980) was used for analysis of Zn and the graphite-atomizer method (ibid., p.283–326, p.585–590 and p.720–741) was employed for analysis of Mn and Cu. The result is summarized in Table 6, which indicates that the present enzyme contains one Zn atom per subunit.

TABLE 6

| Metal | Content (W/V) | Metal/Protein (N/mole) | Metal/Subunit (N/mole) |
|---|---|---|---|
| Zn | 0.21% | 2.13 | 1.05 |
| Mn | Not detected | 0 | 0 |
| Cu | Not detected | 0 | 0 |

6. Effects of various compounds upon enzyme activity

To 50 mM Tris-HCl buffer (pH 7.0) containing the present enzyme, was added each of the compounds being tested to a concentration of 0.1 mM or 1.0 mM. The mixture was incubated at 37° C. for 10 minutes, a sample solution was taken out, and its residual activity was measured according to the procedure described in [Method 1]. The result is shown in Table 7.

TABLE 7

| | Relative Activity (%) Concentraiton (mM) | |
|---|---|---|
| Compound | 0.1 | 1.0 |
| None | — | 100 |
| Semicarbazide hydrochloride | 103 | 91 |
| Phenylmethanesulfonyl fluoride (PMSF) | 86 | 90 |
| p-(Chloromercuri)benzoate (pCMB) | 107 | 90 |
| NaN$_3$ | — | 95 |
| EDTA · 2Na | — | 97 |
| 8-Oxyquinoline | 57 | 66 |
| o-Phenanthroline | — | 95 |
| a,a'-Dipyridyl | — | 92 |
| Diethyldithiocarbamate | 93 | 94 |
| ZnCl$_2$ | 1 | 22 |
| MgCl$_2$ | 87 | 85 |
| CoCl$_2$ | — | 105 |
| AgNO$_3$ | 107 | 41 |
| NiCl$_2$ | — | 90 |

As seen from the table, the present enzyme is slightly inhibited by PMSF and pCMB, and considerably inhibited by 8-oxyquinoline. This is probably because Zn contained in the enzyme in chelated by 8-oxyquinoline which is a powerful metal chelator. On the other hand, EDTA and o-phenanthroline show no inhibitory action, indicating that Zn in the present enzyme is firmly bound to the protein segment. The enzyme is also inhibited by Ag, Mg and Zn, most remarkably by Zn.

7. Isoelectric point

The present enzyme was subjected to isoelectric-focusing by the method of Vesterberg, et al. [O. Vesterberg and H. Svenson, Acta Chem. Scand., 20, 820 (1966)]. Its isoelectric point was found to be at pH 4.56.

8. Absorption spectrum

The protein sample purified to homogeneity, of the present enzyme was analyzed with Hitachi Model-228 Spectrophotometer (purchased from Nissei Sangyo). It showed a single absorption peak at 280 nm, suggesting no colored prosthetic group involved.

9 Amino acid sequence at N-terminal

The protein sample was subjected to Edman degradation using Model-470A Gas-phase Sequencer (product of Applied Biosystems), and the resulting PTH-amino acids were automatically analyzed by means of PTH Analyzer 120A (product of Applied Biosystems) using a C18 column ($\phi$2.1×220 mm; product of Brownlee). The amino acid sequence from N-terminal to the 48th amino acid thus determined is shown below.

Met-Arg-Val-Ile-Phe-Ser-Glu-Asp-His-Lys-Leu Arg-Asn-Ala-Lys-Thr-Glu$^{17}$-Leu-Tyr-Gly-Gly-Glu-Leu-Val-Pro-Pro-Phe-Glu-Ala-Pro-Phe-Arg-Ala-Glu$^{34}$-Ala-Ile-Leu-Ala-Ala-Val-Lys-Glu-(Ala)-Gly-Phe-Asp-(Asp)-Val$^{48}$-

10. Amino acid composition

The protein sample was hydrolyzed with 12N-HCl at 110° C. for 24 hours, and analyzed with Amino Acid Analyzer JLC200-A (product of JEOL, Ltd.). The result is shown in Table 8.

TABLE 8

| Amino Acid(e) | Mole Ratio | Approximated Integer | Note |
|---|---|---|---|
| Asx. | 3.2 | 52 | (a) |
| Thr. | 1.9 | 30 | |
| Ser. | 1.6 | 26 | |
| Glx. | 2.9 | 46 | (b) |
| Pro. | 2.2 | 36 | |
| Gly. | 4.6 | 74 | |
| Ala. | 5.3 | 84 | |
| Cys. | 0.1 | 2 | (c) |
| Val. | 2.4 | 38 | |
| Met. | 0.6 | 10 | |
| Ile. | 1.9 | 30 | |
| Leu. | 2.5 | 40 | |
| Tyr. | 1.2 | 20 | |
| Phe. | 1.8 | 28 | |
| His. | 1.0 | 16 | (d) |
| Lys. | 1.7 | 26 | |
| Arg. | 1.5 | 24 | |
| Total | 36.4 | 582 | |
| Mol. weight | (4,215) | 71,393 | (dalton) |

(a) Mixture of aspartic acid and asparagin;
(b) Mixture of glutamic acid and glutamine;
(c) Cystein (2) or cystine (1);
(d) Basis for calculation;
(e) Tryptophan was not detected.

The new acetylpolyamine amidohydolase of the present invention can be produced by culturing, in a medium, a microorganism belonging to the genus Mycoplana and having an ability to produce the enzyme, collecting the microbial cells from the culture, and recovering said enzyme accumulated within the cells.

As the strain to be used in the present invention, any strain can be used, so long as it belongs to the genus Mycoplana and has an ability to produce said new enzyme. As illustrative examples, may be mentioned *Mycoplana bullata* NCIB9440 and *Mycoplana bullata* FERM BP-1845 [deposited at FRI (Fermentation Research Institute, Agency of Industrial Science and Technology) under the Budapest Treaty on Apr. 9, 1988]. The bacteriological properties of *Mycoplana bullata* are described in Bergey's Manual of Systematic Determination, 2, 1458 (1986).

Any synthetic or natural culture medium containing appropriate carbon sources, nitrogen sources, inorganic salts and other nutrients may be used for the purpose of the present invention. As required, polyamine and/or acetylpolyamine may also be added to the medium to enhance the output of the acetylpolyamine amidohydrolase of the present invention. The pH at the start of cultivation is usually in the range of 5 to 11, preferably 6 to 8, and cultivation is carried out at a temperature in the range of 20° to 45° C., preferably 25° to 35° C. Shaking culture or submerged culture with agitation under such conditions for 10 to 100 hours gives a significant quantity of novel acetylpolyamine amidohydrolase of the present invention accumulated within the grown cells. The cells are collected from the culture by centrifugation.

The enzyme can be extrated from the collected cells by methods commonly used for enzyme extraction, such as cell disruption by Dyno-Mill or ultrasonic treatment, treatment with a lytic enzyme, and autolysis. The enzyme extract thus obtained can be purified by a proper combination of purification techniques commonly used for enzymes, affording purified to homogeneity or partially purified products of the present enzyme.

The present enzyme is useful for the quantitative determination of acetylpolyamine to which it is specific. Because of its smaller $K_m$ values, acetylpolyamine can be hydrolyzed in a short time with a small quantity of the enzyme into the corresponding polyamine. The free polyamine thus formed can be quantitatively determined by HPLC, or by reaction with an oxidase that decomposes it to form hydrogen peroxide, followed by measurement of the amount of reaction product formed or the amount of oxygen consumed. As the oxidase, putrescine oxidase is used when the polyamine is putrescine, cadaverine or spermidine; on the other hand, when the polyamine is spermine or spermidine, polyamine oxidase is used to form putrescine, which is then decomposed by putrescine oxidase. Spermidine can be oxidized by either putrescine oxidase or polyamine oxidase. Action of these oxidases forms quantitatively, hydrogen peroxide, which can be easily determined by known techniques.

The hydrogen peroxide thus formed is allowed to react with the chromogen in the presence of a peroxidase to form a pigment, and the absorbance of the resulting colored solution is measured at the maximum absorption peak of the pigment formed, thereby determining the amount of acetylpolyamine.

When plural types of acetylpolyamine are contained in a sample and two types of oxidases have to be used, hydrogen peroxide formed by the first oxidase is converted to a colorless substance, for example, by the method of Japanese Published Examined Application No. 21517/1987, U.S. Pat. No. 4,416,982, European Patent No. 54358. The second enzyme is then added to decompose the remaining substrate, followed by measurement of the amount of hydrogen peroxide formed.

Quantitative analysis of hydrogen peroxide can be effected by addition of chromogens such as 4-aminoantipyrine and phenol, followed by measurement of the absorbance of the resulting colored solution.

A certain specific embodiment of the present invention is illustrated by the following representative examples.

EXAMPLE 1

Figure 5:
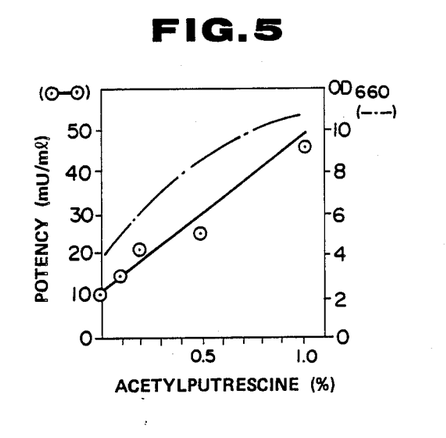
FIG. 5 is a graph showing the relationship between the concentration of acetylputrescine contained in the medium and potency of the cell extract.

At first, 300 ml of a culture medium (pH 7.0) comprising 0.5 g/dl tryptone, 0.5 g/dl yeast extract, 0.05 g/dl sodium chloride, 0.1 g/dl dipotassium hydrogen phosphate, 0.01 g/dl manganese sulfate and 0 to 1.0 g/dl acetylputrescine was put in a 2 l-Erlenmeyer flask and sterilized by heating at 120° C. for 20 minutes *Mycoplana bullata* NCIB9440 was inoculated to the medium and cultured at 28° C. for 2 days. The microbial cells were separated by centrifugation, disrupted by homogenizer, and centrifuged to give a cell extract. The potency of cell extract when varying acetylputrescine concentration in the culture medium is shown in FIG. 5.

EXAMPLE 2

At first, 300 ml of a culture medium (pH 7.0) comprising 0.5 g/dl tryptone, 0.5 g/dl yeast extract, 0.05 g/dl sodium chloride, 0.1 g/dl dipotassium hydrogen phosphate, 0.01 g/dl manganese sulfate and 0.5 g/dl acetylputrescine was put in a 2 l-Erlenmeyer flask and sterilized by heating at 120° C. for 15 minutes. *Mycoplana bullata* NCIB9440 was inoculated into the medium, cultured by shaking at 30° C. for 3 days. The resulting seed culture was transferred to 15 l of a medium having the same composition as above in a 30 l-jar fermenter. After cultivation at 30° C. for 2 days, the thus obtained culture was centrifuged to separate the cells from the culture broth. The cells were washed with physiological saline and suspended in 20 mM phosphate buffer (pH 7.0). After adding glass beads, the suspension was treated with Dyno-Mill KDL (product of W. A. Bachofen) to disrupt the cells. The cell debris suspension was centrifuged and the supernatant was collected as a solution of crude enzyme. Ammonium sulfate was added to the solution of crude enzyme to 80% saturation. A precipitate thus formed was dialyzed against 20 mM phosphate buffer (pH 7.0), the dialyzate was subjected to membrane concentration, and the concentrate was allowed to be adsorbed on DEAE-cellulose packed in a column and previously equilibrated with 20 mM phosphate buffer. After thorough washing with the phosphate buffer, the adsorbed portion was eluted using sodium chloride solutions of different concentration of 0-1 M by linear, concentration-gradient technique. The active fraction was subjected to ammonium sulfate precipitation having 80% saturation, and the collected precipitate was dissolved in a small volume of 50 mM phosphate buffer (pH 7.0). The solution was passed through a column packed with Sephadex G-100 (product of Pharmacia Fine Chemicals) previously equilibrated with the same phosphate buffer and the adsorbed portion was eluted with the same buffer. The active fraction collected was again passed through a hydroxyapatite column equilibrated with 10 mM phosphate buffer (pH 6.8), the active portion adsorbed was eluted, and the active fraction thus collected was freeze-dried, to give 10 mg of partially purified enzyme (purity: approximately 0.05%).

EXAMPLE 3

Quantitative determination of acetylputrescine was performed using the enzyme prepared in Example 2 and putrescine oxidase At first, 50 µl of Acetylputrescine solution of different concentrations was added to a reagent solution having the following composition, the mixture was incubated at 37° C. for 10 minutes, and the absorbance of the resulting colored solution at 500 nm was measured.

Figure 6:
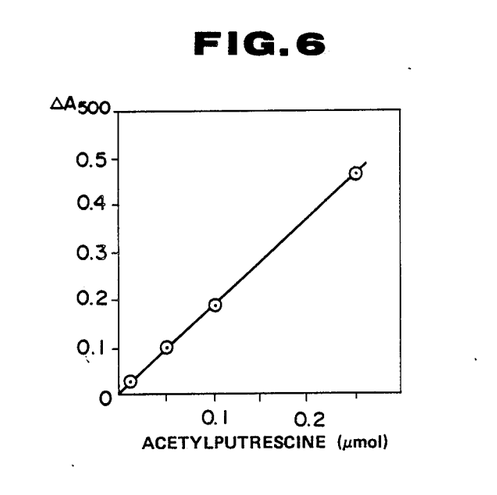
FIG. 6 is a graph showing the linear relationship between the absorbance at 500 nm and acetylputrescine concentration.

The result is shown in FIG. 6. A linear relationship was observed between the absorbance and acetylputrescine concentration, indicating that acetylputrescine can be quantitatively determined by the use of the novel acetylpolyamine amidohydrolase of the present invention.

| (Reagent solution) | |
|---|---|
| 0.1 M Phosphate buffer | 1.5 ml |
| 2.4 mM 4-Aminoantipyrine | 0.5 ml |
| 42 mM Phenol | 0.5 ml |
| Peroxidase | 20 U |
| Acetylpolyamine amidohydrolase prepared in Example 2 | 5 U |
| Putrescine oxidase | 1 U |

EXAMPLE 4

Quantitative determination of $N^1$-acetylspermidine was performed using acetylpolyamine amidohydrolase prepared in Example 2, polyamine oxidase and putrescine oxidase.

Figure 7:
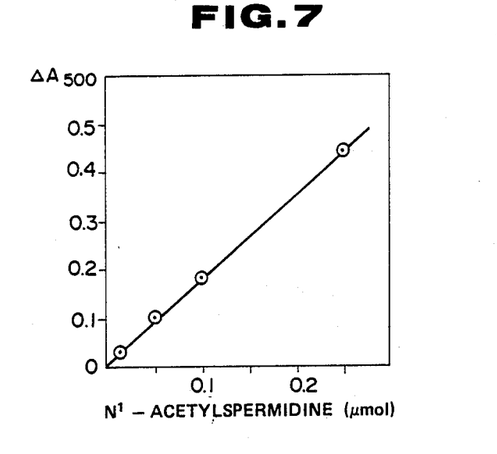
FIG. 7 is a graph showing the linear relationship between the absorbance and $N^1$-acetylspermidine concentration.

To 1.5 ml of a 0.1 mM phosphate buffer were added the enzyme prepared in Example 2 (5 U), polyamine oxidase (1 U), 42 mM phenol solution (0.5 ml) and peroxidase (20 U), and the resulting mixture was further mixed with a solution of $N^1$-acetylspermidine of different concentrations. Incubation was carried out at 37° C. for 5 minutes, and hydrogen peroxide formed was converted into a colorless substance by the above-mentioned method. To the reaction mixture containing putrescine thus formed were added putrescine oxidase (1 U) and 2.4 mM 4-aminoantipyrine (0.5 ml). Incubation was carried out at 37° C. for 10 minutes, and the absorbance of the resulting colored solution at 500 nm was measured. The result is shown in FIG. 7. A linear relationship was observed between the absorbance at 500 nm and concentration of $N^1$-acetylspermidine, indicating that $N^1$-acetylspermidine can be quantitatively determined by the use of the novel acetylpolyamine amidohydrolase of the present invention.

EXAMPLE 5

The total amount of acetylpolyamine, i.e. acetylputrescine, acetylcadaverine, $N^1$-acetylspermidine, $N^8$-acetylspermidine and acetylspermine contained in a sample was quantitatively determined by using the enzyme prepared in Example 2, polyamine oxidase and putrescine oxidase.

To 1.5 ml of a 0.1 M phosphate buffer (pH 7.0) were added acetylpolyamine amidohydrolase prepared in Example 2 (5 U), polyamine oxidase (1 U) 42 mM phenol solution (0.5 ml) and peroxidase (20 U), and the resulting mixture was further mixed with each of samples (0.1 ml, 0.2 ml, 0.3 ml, 0.4 ml and 0.5 ml) and incubated at 37° C. for 5 minutes. Hydrogen peroxide formed was converted into a colorless substance by the above-mentioned method.

Figure 8:
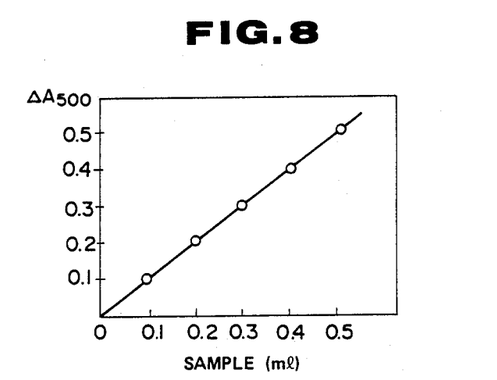
FIG. 8 is a graph showing the linear relationship between the absorbance at 500 nm and the total amount of acetylpolyamine.

To the resulting reaction mixture were added putrescine oxidase (1 U) and 0.5 ml of 2.4 mM 4-aminoantipyrine, and the mixture was incubated at 37° C. for 10 minutes. The absorbance of the resulting colored solution at 500 nm was measured. The result is shown in FIG. 8. A linear relationship was observed between the absorbance and the concentration of polyamine contained in the sample tested. The total amount of polyamine 0.6 μmole, determined by the method of the present invention was in good agreement with the amount measured by HPLC, indicating that the total amount of acetylpolyamine contained in a sample can be quantitatively determined by the use of the novel acetylpolyamine amidohydrolase of the present invention.

EXAMPLE 6

Figure 11:
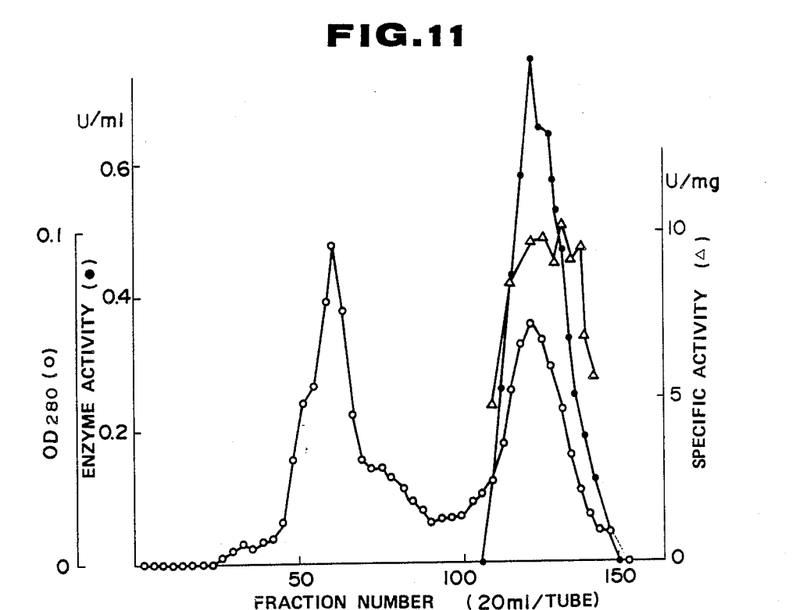
FIG. 11 shows the elution pattern of the product purified to homogeneity of the enzyme of the present invention by ion-exchange chromatography using DEAE-Sepharose Fast Flow.
Figure 12:
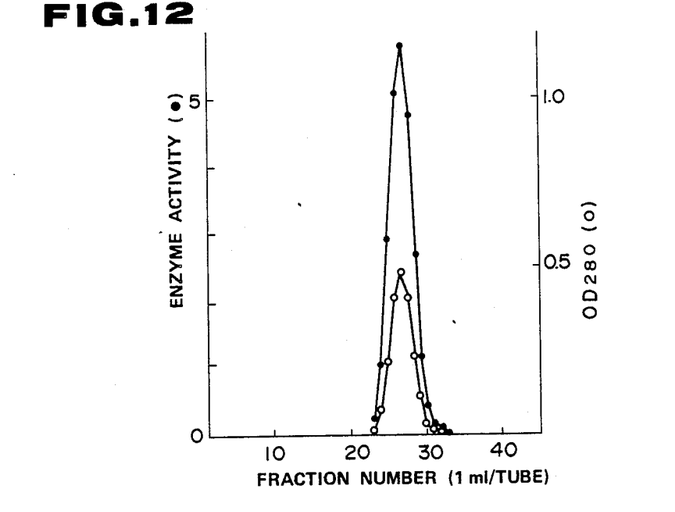
FIG. 12 shows the elution pattern of the product purified to homogeneity of the enzyme of the present invention by gel filtration using Superose prep12 HR 16/50.

At first, 300 ml of a culture medium (pH 7.0) comprising 2.0 g/dl mannitol, 2.0 g/dl polypeptone, 1.4 g/dl Erhlich's meat extract, 1.0 g/dl yeast extract, 0.3 g/dl sodium chloride and 0.05 g/dl manganese sulfate was put in a 2-liter Erlenmeyer flask and sterilized by heating at 120° C. for 15 minutes. *Mycoplana bullata* FERM BP-1845 was inoculated to the medium, was cultured by shaking at 30° C. for 3 days. The master culture thus obtained was inoculated into 15 liters of a medium having the same composition, as described above in a 30 l-jar fermenter, and culturing was carried out at 30° C. for 2 days. The thus obtained culture was subjected to centrifugation to separate microbial cells from a culture broth. The cells were suspended in a 100 mM borate buffer (pH 8.5), and disrupted by Manton-Gaulin homogenizer (product of General Electric). The cell debris suspension thus obtained was centrifuged, and the solution of crude enzyme was collected as a supernatant. The solution was passed through HPA-75 (product of Mitsubishi Kasei Corporation) column previously equilibrated with a 100 mM borate buffer. After thorough washing with the same borate buffer, the adsorbed portion was eluted with the same buffer containing 400 mM ammonium sulfate, the active fraction collected was subjected to membrane concentration, and the concentrate was passed through DEAE-Sepharose Fast Flow (product of Pharmacia Fine Chemicals) column previously equilibrated with a 100 mM borate buffer (pH 8.5) containing 50 mM sodium chloride. After thorough washing with the same buffer, the adsorbed enzyme was eluted with the buffer containing 75 mM sodium chloride, the active fraction collected was subjected to membrane concentration, and the concentrate was passed through Butyl-Toyopearl 650 M (product of Toyo Soda) previously equilibrated with 100 mM borate buffer containing 1 M ammonium sulfate (pH 8.5). After thorough washing with the same buffer, the adsorbed enzyme was eluted by the linear concentration-gradient technique (concentration of ammonium sulfate; from 1 to 0 M). The active fraction collected was concentrated by ultrafiltration, and the concentrate was passed through PD-10 (product of Pharmacia Fine Chemicals) column to exchange the buffer for a fresh one and then charged in DEAE-Sepharose Fast Flow column ($\phi 4.2 \times 38.5$ cm: product of Pharmacia Fine Chemicals) previously equilibrated with 10 mM Tris-HCl buffer (pH 7.0). The column was washed with the same buffer at a flow rate of 293 ml/hr to remove unadsorbed proteins, the adsorbed enzyme was eluted with the same buffer containing 0.1 M sodium chloride, and fractions with specific activity of 8 U/mg or higher were collected as an active fraction. The elution pattern is shown in FIG. 11. This active fraction was concentrated by ultrafiltration by a factor of 37 using YM-10 (product of Amicon) and Centricon-10 (product of Amicon) in that order. Polyacrylamide gel electrophoresis of this concentrate showed sub-bands other than the main band. Hence, the above active fraction was further purified by gel filtration as follows. It was passed through Superose prep12 HR 16/50 column ($\phi 1.6 \times 50$ cm; product of Pharmacia Fine Chemicals) previously equilibrated with a 50 mM Tris-HCl buffer containing 300 mM sodium chloride (pH 7.0), the column was connected to Tri-Rotor II pump (product of Nihon Bunko), and elution was carried out at a flow rate of 30 ml/hr. As shown in FIG. 12, the eluted active fractions showed a plotted curve symmetric with respect to a vertical axis, indicating nearly uniform distribution of specific activity. The fractions were collected as the purified to homogeneity.

Its protein concentration, measured on the basis of spectrophotometric data, assuming $E_{280\,nm}^{1\%}$ was 10.8, was 4.5 mg/ml.

Table 9 summarized purification results for the step using Butyl-Toyopearl and thereafter.

TABLE 9

| Step | Volume (ml) | Total Activity (U) | Total Protein* (mg) | Specific Activity (U/mg) | Yield (%) |
| --- | --- | --- | --- | --- | --- |
| Butyl-Toyopearl | 8 | 334.7 | 323.3 | 1.064 | 100 |
| DEAE-Sepharose | 37 | 248.8 | 23.7 | 10.52 | 74.3 |
| Ultrafiltration | 1 | 157.6 | 12.5 | 12.61 | 47.1 |
| Superose prep 12 | 8 | 123.4 | 9.9 | 12.51 | 36.9 |

*$E_{280\,nm,\,1\,cm}^{1\%} = 10.8$

To further examine the uniformity of the present enzyme, the undenatured sample obtained in this Example was subjected to polyacrylamide gel electrophoresis according to the method of Davis, et al. [B. J. Davis, et al., Ann. N.Y. Acad. Sci., 121, 404 (1964)]. The result showed that the sample was a homogeneous protein. Likewise, the sample was subjected to SDS-polyacrylamide gel electrophoresis in Phast system (product of Pharmacia Fine Chemicals) according to the procedure described in its technical bulletin using Phast Gel 10/15 (product of Pharmacia Fine Chemicals) and LMW calibration kit (product of Pharmacia Fine Chemicals) as molecular weight marker. As the result, the sample of the present enzyme showed a single band, indicating that the sample was a homogeneous protein.

In addition, the sample was subjected to the ultracentrifugal sedimentation analysis according to the method of Svedberg, et al. (T. Svedberg and K. O. Pedersen "The Ultracentrifuge" Oxford Univ. Press, 1946) using Ultracentrifugal Sedimentation Analyzer Model UCA-1A (product of Hitachi Koki) at 20° C. for 60 minutes at a bar angle of 65° and a revolution speed of 55,430 rpm. The sedimentation pattern remained symmetric with the elapse of time, indicating the sample was homogeneous. The sedimentation coefficient, $S_{20,w}$ was calculated by the conventional method to be 5.27S.

The sample purified to homogeneity obtained in this Example was dissolved in 50 mM Tri-HCl buffer (pH 7.0) at a concentration of 4.5 mg/ml, solid ammonium sulfate was slowly added to the solution, and the addition was stopped immediately before the solution became saturated. At that time, the solution came to be slightly turbid. Allowing this turbid solution to stand overnight at 4° C. gave glossy crystals deposited on the bottom of the vessel. The crystals consisted of colorless needless of the same shape having a length of 0.1 to 0.5 mm and a diameter of 0.05 to 0.01 mm.

What is claimed is:

1. A substantially pure acetylpolyamine amidohydrolase which specifically hydrolyzes the amido bond in acetylpolyamine selected from the group consisting of acetylputrescine, acetylcadaverine, acetylspermidine and acetylspermine, wherein the Km value for the acetylpolyamine is 0.31 mM or less.

2. The product purified to homogeneity of the acetylpolyamine amidohydrolase defined by claim 1, having the characteristics described below:
   (i) Molecular weight: 67,000 gel filtration method using high-performance liquid chromatography, having a dimeric structure composed of two subunits of a molecular weight of 36,000 by SDS-polyacrylamide gel electrophoresis;
   (ii) isoelectric point: 4.56 by isoelectricfocusing,
   (iii) optimum pH: at pH 9 for acetylputrescine and acetylspermidine, at about pH 8 for acetylcadaverine, and at pH 10 for acetylspermine
   (vi) optimum temperature: 60° C. when using any of acetylputrescine, acetylcadaverine, acetylspermidine and acetylspermine as substrate; and
   (v) inhibitor: it is inhibited by $Zn^{2+}$, 8-oxyquinoline and $Ag^+$.

3. A method for quantitative determination of acetylpolyamine contained in a sample, which comprises exposing the sample to the action of the acetylpolyamine amidohydrolase defined by claim 1 to thereby hydrolyze the amido bond in acetylpolyamine, and determining the amount of the polyamine thus formed.

4. A process for producing the acetylpolyamine amidohydrolase defined by claim 1, which comprises culturing a microorganism belonging to the species *Mycoplana bullata* in a medium, collecting microbial cells from the culture, and recovering acetylpolyamine amidohydrolase accumulated within the cells.

* * * * *

UNITED STATES PATENT AND TRADEMARK OFFICE
CERTIFICATE OF CORRECTION

PATENT NO. : 4,981,788
DATED : January 1, 1991
INVENTOR(S) : TAKAYUKI UWAJIMA, ET AL.

It is certified that error appears in the above-identified patent and that said Letters Patent is hereby corrected as shown below:

COLUMN 2

Line 14, "X, △ , ▢ and" should read -- ⊙, X, △ , ▢ and--.
    Line 15, "acetylcadaveri $N^1$-" should read
          --acetylcadaverine, $N^1$- --.
    Line 60, "known The" should read --known. The--.

COLUMN 18

Line 25, "67,000 gel" should read --67,000 by gel--.

Signed and Sealed this

Eighth Day of September, 1992

*Attest:*

DOUGLAS B. COMER

*Attesting Officer*      *Acting Commissioner of Patents and Trademarks*